(12) United States Patent
Helmer et al.

(10) Patent No.: US 9,336,690 B2
(45) Date of Patent: May 10, 2016

(54) TRAINING MECHANISM FOR DRUG DELIVERY DEVICE

(75) Inventors: Michael Helmer, Frankfurt am Main (DE); Peter Nober, Rommersheim (DE); Christoph Garthen, Dexheim (DE); Christian Dexheimer, Langen (DE); Benjamin Schaefer, Bischoffen (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 540 days.

(21) Appl. No.: 13/989,881

(22) PCT Filed: Dec. 6, 2011

(86) PCT No.: PCT/EP2011/071845
§ 371 (c)(1),
(2), (4) Date: Aug. 19, 2013

(87) PCT Pub. No.: WO2012/076494
PCT Pub. Date: Jun. 14, 2012

(65) Prior Publication Data
US 2015/0302778 A1   Oct. 22, 2015

(30) Foreign Application Priority Data
Dec. 6, 2010 (EP) .................................. 10193755

(51) Int. Cl.
*G09B 23/28* (2006.01)
*A61M 5/24* (2006.01)
*A61M 5/315* (2006.01)

(52) U.S. Cl.
CPC .......... *G09B 23/285* (2013.01); *A61M 5/31505* (2013.01); *G09B 23/28* (2013.01); *A61M 5/24* (2013.01); *A61M 5/31511* (2013.01); *A61M 5/31513* (2013.01); *A61M 2005/31508* (2013.01)

(58) Field of Classification Search
USPC ........................ 434/262, 267, 268, 272, 275
See application file for complete search history.

(56) References Cited

U.S. PATENT DOCUMENTS

| | | | | |
|---|---|---|---|---|
| 3,318,021 A | * | 5/1967 | Sarnoff | G09B 23/285 434/262 |
| 3,426,448 A | * | 2/1969 | Sarnoff | G09B 23/285 434/262 |

(Continued)

FOREIGN PATENT DOCUMENTS

| | | |
|---|---|---|
| EP | 2180459 | 4/2010 |
| GB | 2195808 | 4/1988 |
| WO | 02/04049 | 1/2002 |

OTHER PUBLICATIONS

International Search Report for Int. App. No. PCT/EP2011/071845, completed Feb. 15, 2012.

*Primary Examiner* — Kurt Fernstrom
(74) *Attorney, Agent, or Firm* — McDonnell Boehnen Hulbert & Berghoff LLP

(57) ABSTRACT

The present invention relates to a cartridge for a drug delivery device comprising of a body of substantially cylindrical shape, a piston slidably disposed in the body along two opposite axial directions, along a distal and along a proximal direction, and at least one friction means operably engaged with the piston to generate a pre-defined friction force between the piston and an inside wall of the body, when the piston is displaced relative to the body, wherein in response to an axial displacement of the piston relative to the body in distal direction and in proximal direction, the at least one friction means is adapted to generate respective proximal and distal friction forces that are different in magnitude.

12 Claims, 3 Drawing Sheets

(56) References Cited

U.S. PATENT DOCUMENTS

| | | | | |
|---|---|---|---|---|
| 3,795,061 A | * | 3/1974 | Sarnoff | G09B 23/285 434/262 |
| 5,037,306 A | * | 8/1991 | van Schoonhoven | G09B 23/285 434/262 |
| 5,071,353 A | * | 12/1991 | van der Wal | G09B 23/285 434/262 |
| 5,567,160 A | * | 10/1996 | Massino | G09B 23/285 434/262 |
| 7,682,155 B2 | * | 3/2010 | Raven | G09B 23/285 434/262 |
| 2002/0168618 A1 | | 11/2002 | Anderson et al. | |
| 2007/0111175 A1 | * | 5/2007 | Raven | G09B 23/285 434/262 |
| 2012/0015335 A1 | * | 1/2012 | Smith | G09B 23/285 434/262 |
| 2012/0015336 A1 | * | 1/2012 | Mach | G09B 23/285 434/262 |
| 2015/0235571 A1 | * | 8/2015 | Alexandersson | A61M 5/31501 434/262 |

* cited by examiner

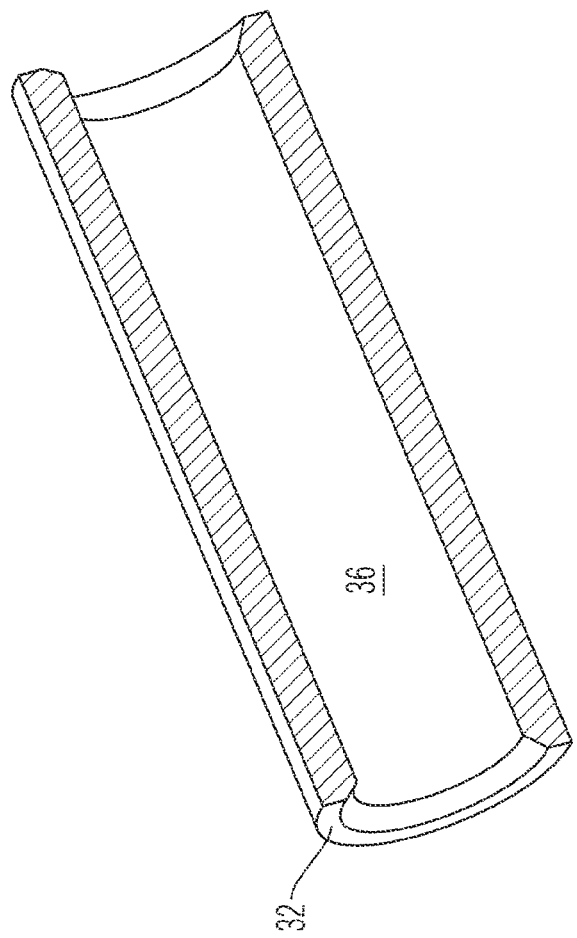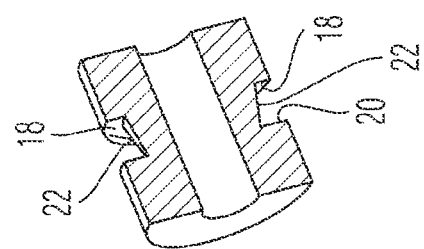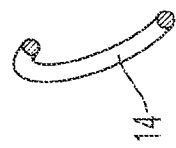
Fig. 4

TRAINING MECHANISM FOR DRUG DELIVERY DEVICE

CROSS REFERENCE TO RELATED APPLICATIONS

The present application is a U.S. National Phase Application pursuant to 35 U.S.C. §371 of International Application No. PCT/EP2011/071845 filed Dec. 6, 2011, which claims priority to European Patent Application No. 10193755.5 filed Dec. 6, 2010. The entire disclosure contents of these applications are herewith incorporated by reference into the present application.

FIELD OF THE DISCLOSURE

The present invention relates to a mechanical training mechanism for a drug delivery device that allows a user to get trained and to become accustomed to the handling of a drug delivery device without the necessity of administering a dose of a medicinal product or placebo, e.g. by injection. The training mechanism is universally adapted to be implemented in a cartridge, in particular in a training or test cartridge for a drug delivery device as well as in the device itself.

BACKGROUND

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe.

Pen-type injectors of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Since such drug delivery devices are to be used in a home environment and in particular by way of self-medication, the user or patient has to become accustomed to the handling of the device prior to self-administering a dose of the medicament.

Particularly for the purpose of training or testing a device and its properties, there exist various training cartridges or syringes to be operably coupled with a drive mechanism of a drug delivery device. When appropriately coupled with the drive mechanism, the training cartridge should provide a realistic feedback to the user on how the drug delivery device and its mechanical components behave during dose setting and dose dispensing procedures.

In a rather simple approach, training cartridges are filled with water or a placebo featuring comparable mechanical properties than the genuine medicinal product originally contained in the cartridge.

Even though such water- or placebo-filled cartridges may provide realistic mechanical feedback of the cartridge itself and for the drug device's drive mechanism and since these known cartridges also mimic the visible behaviour of the cartridge, such dummy cartridges might be accidentally confused with genuine cartridges filled with a medicinal product. Consequently, the patient may inject water or placebo instead of the prescribed drug and may thus be treated with an incorrect amount of the medicament.

Furthermore, when making use of water- or placebo-filled cartridges, any of such training or dummy cartridges must be sterile filled or terminally sterilized in case the contents are injected. This also means that the training or dummy cartridge can only be used by a single user in order to prevent any potential cross-contamination of the cartridge, which may happen if a cartridge would be used by several users. Moreover, such water- or placebo-filled cartridges have to be used up within a given shelf life or within their given in-use life.

Cartridges being filled with either a placebo or with a medicament, the effect can be observed, that the displaceable piston is to be pushed or pulled in axial direction with push- or dragging forces of different magnitude. For instance, pushing the piston in distal direction for expelling the liquid content of the cartridge requires a pressure being substantially greater than a force required for returning and pulling the piston back into its initial position. When designing a training cartridge without a liquid content, also this non-symmetric actuating force should be simulated in a realistic way.

It is therefore an object of the present invention to provide a training cartridge to be used with a drug delivery device requiring different actuating forces for different modes of operation. Hence, the training or test cartridge should be able to simulate the overall behaviour of a genuine cartridge to a large extend. Preferably, the training cartridge should not require filling with water or a placebo. Moreover, it is intended to provide a reset function for the training cartridge allowing to make use of said cartridge multiple times.

SUMMARY

In a first aspect, the invention provides a training or test cartridge for a drug delivery device. The cartridge comprises a body of substantially cylindrical shape. The cartridge further has a piston slidably disposed in the body along two opposite axial directions, that is, along the longitudinal axis of the cylindrical body or barrel. These two opposite axial directions are in the following denoted as distal and proximal direction. Generally, a displacement of the piston in distal direction refers to an expelling of the medicament disposed therein whereas a displacement in opposite, hence proximal direction corresponds to a draw-up of a medicament into the body or barrel.

The cartridge further comprises at least friction means being operably engaged with the piston to generate a pre-defined friction force between the piston and an inside wall of the body when the piston is displaced relative to the body. Hence, The at least one friction means serves to provide a dynamic or sliding friction of the piston inside the body of the cartridge. The at least one friction means is further adapted to generate distal and proximal friction forces that are different in magnitude. Hence, in response to a distally directed displacement of the piston relative to the body, the at least one friction means is adapted to generate a distal friction force and in response to an opposite relative displacement, hence in proximal direction, the friction means is adapted to generate a proximal friction force, which is different in magnitude compared to the distal friction force.

By way of the at least one friction means, direction dependent friction forces of different magnitude can be provided, thus allowing to simulate different actuating forces to be applied to the piston for expelling the medicament or for drawing the medicament into the barrel. This way, the aspect of different, direction specific actuating forces can be taken into consideration without the necessity of actually filling the cartridge with a liquid substance.

According to a preferred aspect, the friction means comprises at least a friction member slidably disposed in axial direction in at least one receptacle of the piston. Depending on the direction of a relative displacement between piston and body of the cartridge, the friction member itself may experience a respective axial displacement relative to the piston. In particular, if the piston is displaced in distal direction, the friction member will initially move in proximal direction relative to the piston. In another scenario, if the piston is displaced in proximal direction, the friction member will move in distal direction relative to the piston inside the piston's receptacle, initially.

Consequently and according to another preferred embodiment, the axial expansion of the receptacle of the piston is larger than the axial dimension or axial cross section of the friction member, thus allowing for a relative axial displacement of the friction member to the piston. Furthermore, the receptacle of the piston is open in radial direction towards the inside wall of the body. This way, the friction member disposed in said receptacle can remain in mechanical or frictional engagement with the inside wall of the body.

If for instance the piston is displaced in axial direction, by a sliding friction of friction member and inside wall of the body, the friction member itself will be reluctant to follow this motion but tends to remain in its initial position relative to the body. It is due to its inertia and/or to an inherent friction of friction member and inside facing wall of the body, that the friction member tends to remain in an initial position and finally becomes subject to a relative displacement with respect to the moving piston.

In the course of a movement of the piston, the friction member will finally be trailed or drawn by the piston in the same direction the piston moves.

According to another preferred embodiment, the radial size of the receptacle adapted to receive the friction member, varies in axial direction. In particular, a bottom section of the receptacle extends at an angle with respect to the axial direction. For instance, the bottom section of the receptacle may be somewhat wedge-shaped. Therefore, when displaced relative to the piston the friction member becomes subject to a varying radially directed squeezing between the bottom section of the receptacle and the inside facing side wall of the body of the cartridge.

If for instance the radial depth of the receptacle is smaller than the radial expansion or dimension of the friction member, said friction member will experience a radially outwardly directed pressure and may thus induce an increased friction force to the inside wall of the piston. If, however, the friction member is disposed in a position of the receptacle featuring a greater radial depth, respective radially directed friction forces will be reduced in magnitude, thus providing reduced friction to the inside wall of the body.

According to another preferred embodiment, the receptacle comprises a distal and a proximal stop face for the friction member. If the piston is displaced in distal direction with respect to the body, the proximal stop face serves as an abutment face for the at least one friction member. If the piston is displaced in opposite direction, the proximal stop face provides a comparable abutment for the friction member. By means of proximal and/or distal stop face, the friction member disposed in the receptacle is slidably displaced in the body of the cartridge in form of a kind of trailing or drawing motion.

According to a further preferred embodiment, the bottom section of the receptacle from the distal stop face towards the proximal stop face is slanted or skewed in a radial outward direction. This way, radial depth of the receptacle is greater towards the distal stop face than towards the proximal stop face. Hence, the friction member disposed in the receptacle is shifted radially outwardly when in proximal stop position and shifts radially inwardly when reaching a distal stop position. This way, the actuation force required to displace the piston relative to the cartridge becomes larger in distal direction than the oppositely directed force required for displacing the piston in proximal direction relative to the cartridge.

Accordingly, radial depth or radial dimensions of the receptacle and corresponding radial dimensions of the friction member are mutually adapted in such a way, that the radial expansion of the distal stop face of the receptacle is greater than the radial dimension of the friction member and/or that the radial expansion of the proximal stop face of the receptacle is smaller or equal than the radial dimension of the friction member. In this way, it can be provided, that the friction member radially abuts with the inside wall of the body of the cartridge when said friction member is in its proximal end position, which typically occurs, when the piston is displaced in distal direction relative to the body of the cartridge.

Further, it is generally conceivable, that the piston comprises several receptacles arranged at different locations at the outer or radial circumference of the piston. Each receptacle may be individually provided with at least one friction member slidably disposed therein.

According to another preferred embodiment, the piston of the cartridge comprises a receptacle comprising an annular groove adapted to receive a respective annular ring. Accordingly, the friction member then comprises an annular ring to be slidably disposed in said annular groove. Preferably, the ring comprises a slit allowing to modify the diameter and the radial extension of the ring. This way, the ring itself may change in diameter, in particular when it is displaced between proximal and distal end faces of the receptacle. This modification of the ring geometry can be due to the slanted bottom section of the receptacle staying in abutment with an inside facing portion of the slit ring.

Preferably, the ring comprises an O-ring and is made of an elastically deformable material. Practically, the ring is made of a thermoplastic material or of synthetic or natural rubber, thus inherently providing a well-defined friction effect.

The illustrated mechanism is described with respect to a cartridge but can be universally applied and implemented in a drug delivery device comprising a respective hollow cylindrical body portion to receive a piston slidably displaced therein. Then, a training device can even be provided without having a cartridge disposed therein. The drug delivery device then at least comprises: a body portion of substantially cylindrical shape and a a piston slidably disposed therein along two opposite axial directions, namely along a distal and along a proximal direction. The device further comprises at least one friction means operably engaged with the piston to generate a pre-defined friction force between the piston and an inside wall of the body portion when the piston is displaced relative to the body, wherein in response to an axial displacement of the piston relative to the body portion in distal direction and in proximal direction, the at least one friction means is adapted to generate respective proximal and distal friction forces that are different in magnitude.

With this embodiment, it is typically suggested that a drive mechanism of the drug delivery device is operably engaged with a displaceable piston. Since known drive mechanisms of e.g. pen-type injectors typically comprise an axially displaceable piston rod adapted to interact with a piston of a cartridge, the piston rod may comprise a radially widened piston section at a distal end adapted to frictionally engaged with an inside facing wall of the body portion.

Generally, all further embodiments described and illustrated with respect to a cartridge can be universally applied and adapted to a respective drug delivery device.

In still another independent aspect, the invention further relates to a drug delivery device for dispensing of a dose of a medicinal fluid. The drug delivery device comprises a housing, a cartridge holder and a drive mechanism, wherein the cartridge as described above is to be disposed in the cartridge holder and is to be operably engaged with the drive mechanism. In particular, the drive mechanism comprises a piston rod to be axially displaced in both, proximal and distal direction. The piston rod is further to be operably engaged with the piston of the cartridge in order to induce distally and/or proximally directed displacement to the piston.

The training cartridge may also be integrated into a drug delivery device and may imitate the form of a conventional barrel of a syringe or of comparable injection devices. Moreover, the cartridge may imitate the design of a vial, carpule or ampoule and may be replaceably disposed in a drug delivery device, such like a pen-type injector.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, a preferred embodiment of the invention will be described in greater detail by making reference to the drawings in which:

FIG. 4 depicts the configuration according to FIG. 3 in cross section.

DETAILED DESCRIPTION

In FIGS. 1 to 4, the cartridge is illustrated in a simplified way as a hollow cylindrical body 32 having a piston 10 slidably disposed therein. The piston 10 acts as a sealing member and serves to provide a liquid tight seal for the cartridge. The body 32 is typically made of glass or some other material being inert to the medicament to be disposed and stored therein. Since the present cartridge is exclusively designed for training purposes, the body might be made of a different material, e.g. transparent plastic.

Figure 1:
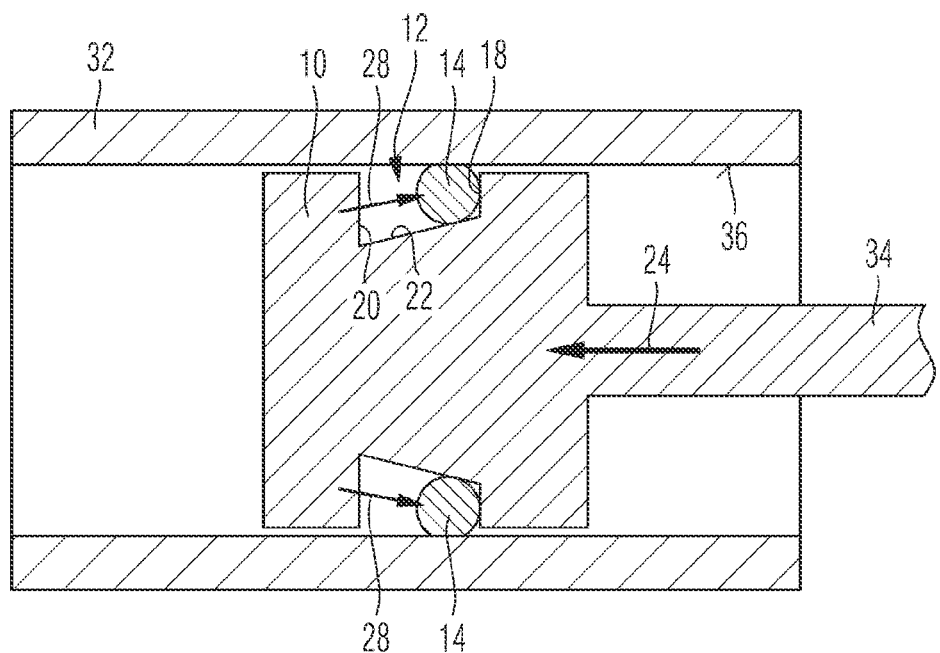
FIG. 1 schematically illustrates the cartridge during a distally directed displacement of its piston, FIG. 2 schematically illustrates the cartridge according to FIG. 1 during a proximal displacement of the piston.
Figure 2:
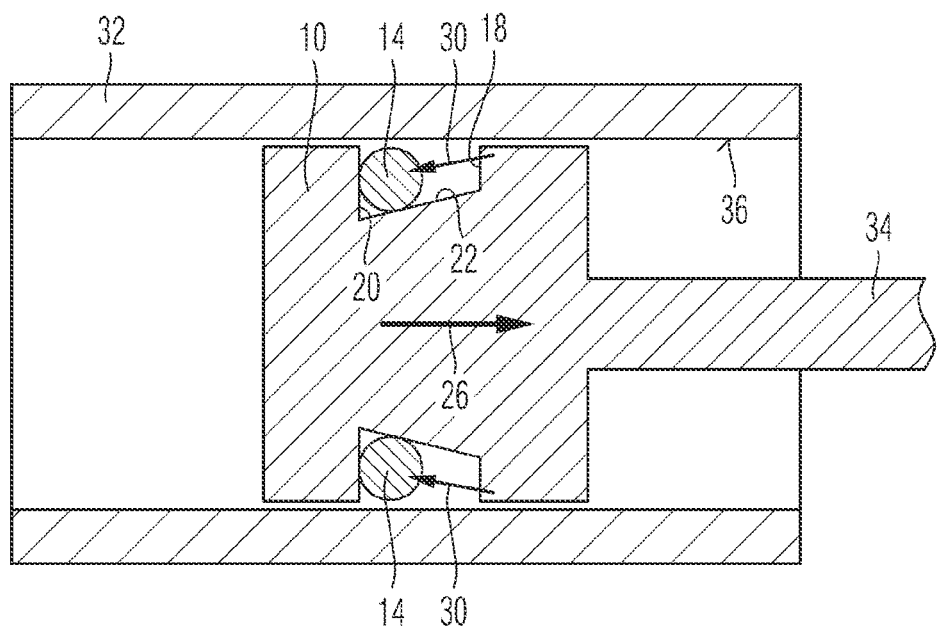

As illustrated in FIGS. 1 through 5, the piston 10 comprises an annular groove 12 having a somewhat wedge-shaped geometry. As illustrated in FIGS. 1 and 2, the groove 12 comprises a distally located stop face 20 and an opposite, proximally located stop face 18. The radial expansion of the distal stop face 20 is larger than the respective radial expansion of the proximal stop face 18. Therefore, a bottom section 22 of the receptacle 12 that stretches from the distal stop face 20 to the proximal stop face 18 extends at a certain angle with respect to the axial direction represented by arrows 24, 26 pointing in distal or proximal direction, respectively.

As further illustrated in FIG. 1, the radial size of the proximal stop face 18 is substantially equal or even smaller than the diameter of the cross section of the ring 14. Hence, the ring 14 made of elastically deformable material is at least slightly squeezed in radial direction and therefore exerts enlarged dynamic or sliding friction forces towards the inside wall 36 of the body 32 of the cartridge as illustrated in FIG. 1. Consequently, when the piston 10 is displaced in distal direction 24, a comparatively large friction force between the ring 14 and the inside wall 36 of the body 32 is generated.

If the schematically illustrated piston rod 34 operably engaged with the piston 10, is moved in a different direction, that is in direction 26 as illustrated in FIG. 2, the ring 14 will be drawn or trailed by the opposite, hence distal end face 20 of the receptacle 12. Since the annular groove 12 features a larger radial depth in proximity to its distal stop face 20, the ring 14 is no longer radially squeezed. At least it experiences a reduced radially outwardly directed pressure and therefore exerts correspondingly reduced dynamic friction towards the inside wall 36. Consequently, an actuation force required to displace the piston 10 in proximal direction 26 is smaller than the force required to move the piston 10 in distal direction relative to the body 32 of the cartridge as depicted in FIG. 1.

Once a distally directed displacement of the piston 10 relative to the body 32 stops and the piston is moved in opposite, hence proximal direction 26 as illustrated in FIG. 2, at the beginning of such an opposite displacement of the piston 10, the O-ring 14 becomes subject to a substantially distally directed displacement 30 relative to the piston 10 until it abuts with the distal stop face 20.

Accordingly, when a distally directed displacement of the piston 10 is conducted for the first time, the O-ring 14 initially moves from a distal end face 20 towards a proximal end face 18 in substantially proximal direction 28 relative to the piston 10 as depicted in FIG. 1.

Figure 3:
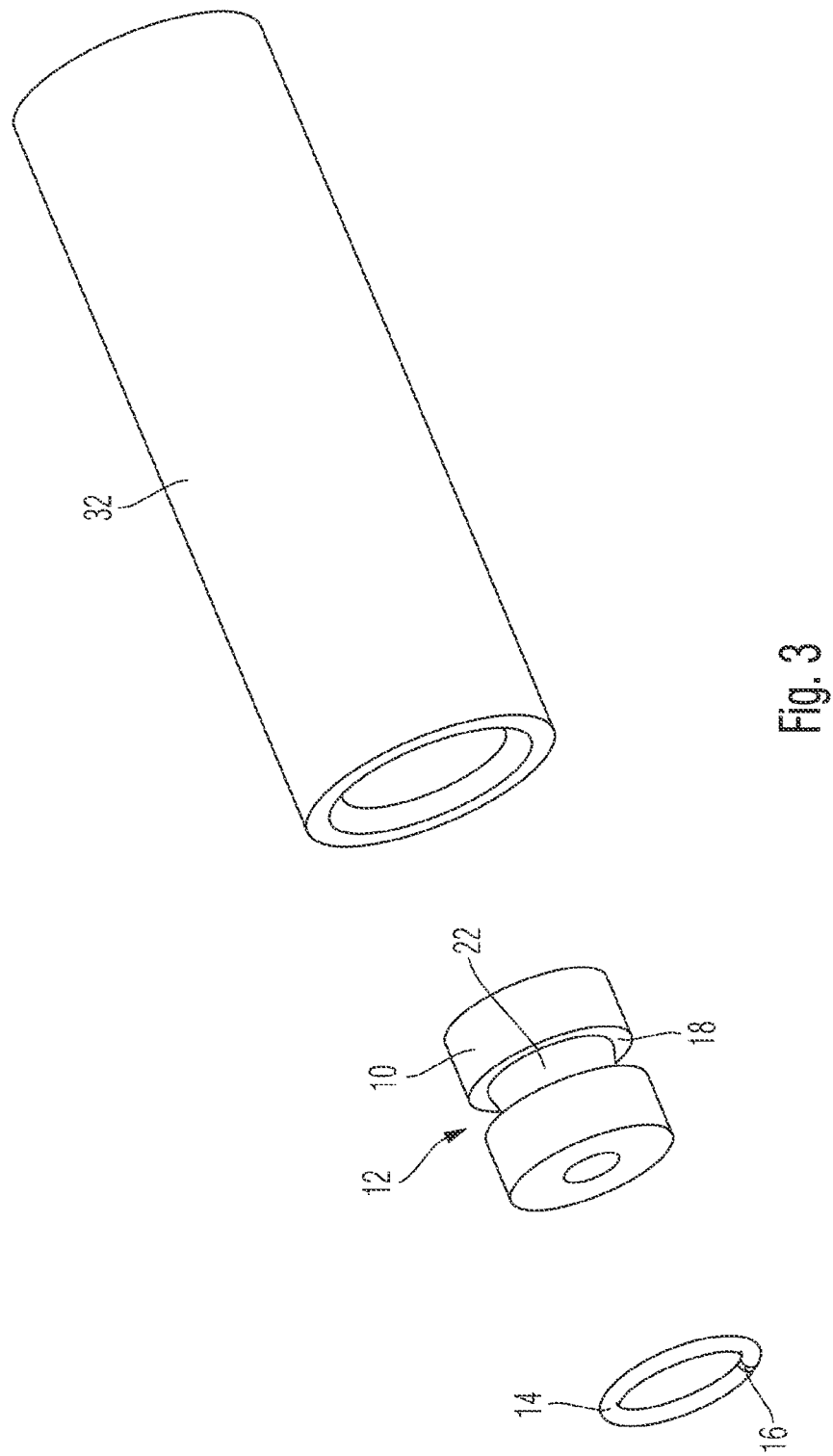
FIG. 3 shows an exploded perspective illustration of the cartridge, its piston and an O-ring disposed in the piston's annular groove

In the sketch of FIG. 3, the slit 16 of the O-ring 14 is further illustrated. By way if the slit 16 the O-ring 14 can be easily adapted to different radii when in distal stop position according to FIG. 2 or when in proximal stop position according to FIG. 1.

The invention claimed is:

1. A cartridge for a drug delivery device comprising:
    a body of substantially cylindrical shape,
    a piston slidably disposed in the body along two opposite axial directions, along a distal and along a proximal direction,
    at least one friction means operably engaged with the piston to generate a pre-defined friction force between the piston and an inside wall of the body, when the piston is displaced relative to the body,
    wherein in response to an axial displacement of the piston relative to the body in distal direction and in proximal direction, the at least one friction means is adapted to generate respective proximal and distal friction forces that are different in magnitude,
    wherein the friction means comprises at least one friction member slidably disposed in axial direction in at least one receptacle of the piston.

2. The cartridge according to claim 1, wherein the axial expansion of the receptacle is larger than the axial dimension of the friction member and wherein the receptacle is open in radial direction towards the inside wall of the body.

3. The cartridge according to claim 1, wherein the radial size of the receptacle varies in axial direction.

4. The cartridge according to claim 1, wherein a bottom section of the receptacle extends at an angle with respect to the axial direction.

5. The cartridge according to claim 1, wherein the receptacle comprises a distal and a proximal stop face for the friction member.

6. The cartridge according to claim 5, wherein the bottom section extends radially outwardly from the distal stop face towards the proximal stop face.

7. The cartridge according to claim 5, wherein the radial expansion of the distal stop face is greater than the radial dimension of the friction member and/or wherein the radial expansion of the proximal stop face is smaller than the radial dimension of the friction member.

8. The cartridge according to claim 1, wherein the receptacle comprises an annular groove.

9. The cartridge according to claim 1, wherein the friction member comprises an annular ring slidably disposed in the groove in axial direction.

10. A drug delivery device for dispensing of a dose of a medicinal fluid, comprising:
   a housing,
   a cartridge holder,
   a drive mechanism, and
   a cartridge according to claim 1, wherein the cartridge is disposed in the cartridge holder and wherein the cartridge is operably engageable with the drive mechanism.

11. The drug delivery device according to claim 10, wherein a piston rod of the drive mechanism is operably connectable with the piston of the cartridge for slidably displacing the piston in axial and/or proximal direction relative to the body of the cartridge.

12. A training device to simulate the mechanical behaviour of a drug delivery device, comprising:
   a body portion of substantially cylindrical shape,
   a piston slidably disposed in the body portion along two opposite axial directions, along a distal and along a proximal direction,
   at least one friction means operably engaged with the piston to generate a pre-defined friction force between the piston and an inside wall of the body portion, when the piston is displaced relative to the body portion,
   wherein in response to an axial displacement of the piston relative to the body portion in distal direction and in proximal direction, the at least one friction means is adapted to generate respective proximal and distal friction forces that are different in magnitude.

\* \* \* \* \*